(12) United States Patent
Scholz

(10) Patent No.: US 7,473,901 B2
(45) Date of Patent: Jan. 6, 2009

(54) APPARATUS FOR MEDICAL IMAGING WITH TWO DETECTOR SYSTEMS

(75) Inventor: Hans-Peter Scholz, Hemhofen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/761,517

(22) Filed: Jun. 12, 2007

(65) Prior Publication Data

US 2007/0290138 A1    Dec. 20, 2007

(30) Foreign Application Priority Data

Jun. 12, 2006   (DE) .................. 10 2006 027 221

(51) Int. Cl.
*G01T 1/164* (2006.01)

(52) U.S. Cl. ................................ 250/363.08

(58) Field of Classification Search ............ 250/363.01, 250/363.02, 363.03, 363.04, 363.05, 363.06, 250/363.07, 363.08, 363.09; 378/65, 108, 378/109, 110, 111, 112, 145, 146, 9, 15, 378/19
See application file for complete search history.

(56) References Cited

U.S. PATENT DOCUMENTS 5,608,221 A * 3/1997 Bertelsen et al. ....... 250/363.03
5,629,971 A * 5/1997 Jones et al. .................. 378/145
6,760,399 B2 * 7/2004 Malamud ........................ 378/9
2004/0213371 A1* 10/2004 Bruder et al. ................... 378/9
2006/0067468 A1* 3/2006 Rietzel ......................... 378/65

FOREIGN PATENT DOCUMENTS

WO    WO 02/26134    4/2002

* cited by examiner

*Primary Examiner*—David P Porta
*Assistant Examiner*—Kiho Kim
(74) *Attorney, Agent, or Firm*—Schiff Hardin LLP

(57) ABSTRACT

An apparatus for medical imaging has a first detector system with a first radiation source for emission of first detection radiation, a first acquisition device for acquisition of the first detection radiation, and a first detection region that transversely penetrates an open space in the apparatus that opens at one side of the apparatus. The first detector system can be moved in the circumferential direction of the open space by a movement device. In order to enlarge the usable region of the apparatus, the apparatus has a second detector system with a second detection region that is offset in the longitudinal direction of the axis of the open space relative to the first detection region.

2 Claims, 2 Drawing Sheets

APPARATUS FOR MEDICAL IMAGING WITH TWO DETECTOR SYSTEMS

BACKGROUND OF THE INVENTION

1. Field of the Invention

The present invention concerns a medical imaging apparatus of the type having two detector systems.

2. Description of the Prior Art

X-ray imaging is a proven examination modality in medical diagnostics, wherein a detector system is used for organ examination. A known example is a computed tomography apparatus (CT apparatus), which has a detector system (comprising a radiation source for emission of a detection radiation and an acquisition device) can be moved around an axis that proceeds through an open space between the radiation source and the acquisition device, in which a patient can be positioned.

An apparatus of this type enables a scanning of the organ of the patient and a representation of an image on a film or a display.

In order to achieve scan times in the sub-second range with a CT apparatus, it is known to provide two detector systems that each emit and detect radiation in the same geometric plane. This enabled graphically presentation of moving organs (for example a beating heart). For this purpose, the apparatus is designed with an acquisition device with 64 lines that covers only a z-depth of approximately 4 cm. Acquisition devices with fewer lines cover even smaller dimensions in the z-direction.

SUMMARY OF THE INVENTION

An object of the present invention is to enlarge the usable region in an apparatus of the types described above. This allows graphical depiction a larger region so that different or larger body parts or organs can be graphically represented. An increase of the capability of the apparatus is also achieved.

In a first embodiment of the invention, the above object is achieved by an apparatus for medical imaging having a first detector system with a first radiation source that emits first detection radiation and a first acquisition device that detects the first detection radiation, the first detector system having a first detection region that transversely penetrates an open space in the apparatus that is open at one side of the apparatus, the first detector system being movable in a circumferential direction of the open space by a movement device, and wherein the apparatus further has a second detector system having a second radiation source that emits second detection radiation and a second acquisition device that detects the second detection radiation, and having a second detection region that transversely penetrates the open space, the second detector system also being movable in the circumferential direction of the open space by a movement device, and wherein the second detection region is offset in the longitudinal direction of a longitudinal axis of the open space relative to the first detection region.

The above object is also is achieved in accordance with the present invention in a further embodiment of the apparatus that corresponds to the above-described embodiment but, instead of the second detection region being offset in the longitudinal direction of the longitudinal axis of the open space relative to the first detection region, the first and second detector systems are offset in the longitudinal direction by a displacement device, and can each be fixed at respective displaced positions along the longitudinal axis.

Both embodiments have in common the use of two detector systems whose detection region that extends transversely in the longitudinal region of the examination space for the patient. The detector systems and/or their detection regions can be offset relative to one another in the longitudinal direction of the axis of the open space or can be adjustable in the longitudinal direction of the axis by a displacement device interacts with at least one of the detector systems, and can be lockable in the offset position.

Both inventive embodiments enable offset or larger regions of the body to be detected so as to be graphically represented in the longitudinal direction of the axis of the open space. The detection regions can exhibit an axial separation from one another, or can overlap one another. It is also possible to axially offset the axially-adjustable detection systems in selected regions, and such a displacement is also possible with the regions completely overlapping one another, so that such a displacement can be considered as transverse to the axis.

The design is simplified when the detector systems can be displaced around the axis of the open space into a position in which they enclose between them an angle of approximately 90°. When offset or rotated in the circumferential direction, the radiation sources and acquisition devices of the detector systems can be arranged next to one another (parallel) to each other and such that they can also be moved in the longitudinal direction of the axis of the open space in the second embodiment case.

For movement in the displacement region, a drive motor can operate the displacement device to make the displacement wholly automatic or semi-automatic. The drive motor can be controlled or regulated with an associated control or regulation device.

DESCRIPTION OF THE PREFERRED EMBODIMENTS

Figure 2:
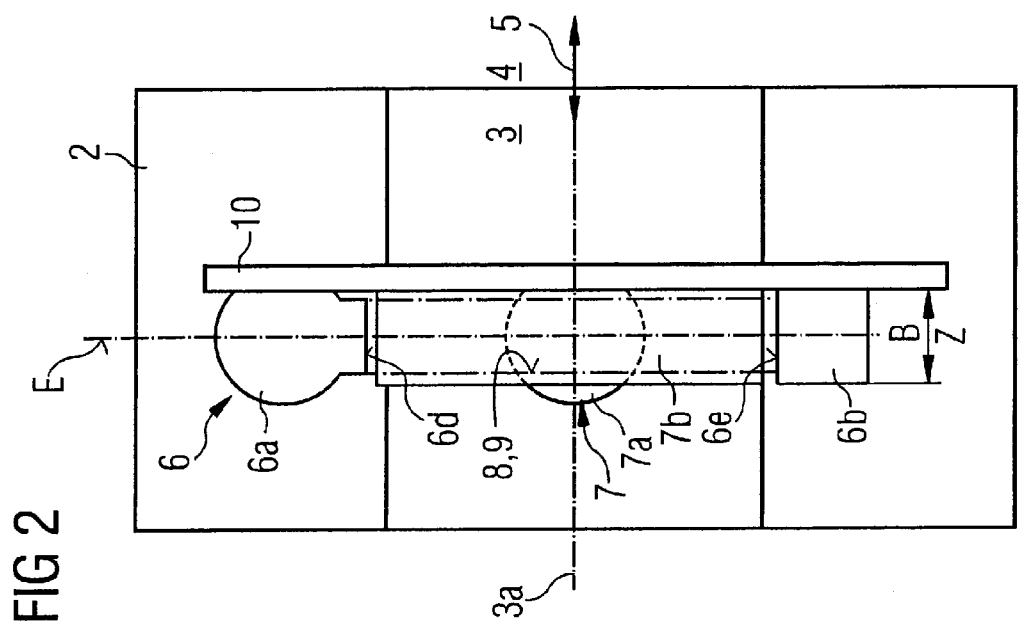
FIG. 2 shows the apparatus in side view.

The apparatus (designated in its entirety with 1) is advantageously a computed tomography apparatus (CT apparatus) that has a frame 2 or housing having a middle region with an open space 3 that is open toward the front side 4 of the apparatus 1 and thus is accessible from the front side 4. A patient can be inserted into the open space 3 by a support table 5 (on which the patient lies) that can be displaced along the center axis of the open space 3. The open space 3 can be, for example, hollow-cylindrical or hollow-elliptical in terms of its vertical cross-section). A drive (not shown) for the support table 5 can serve for the insertion of the support table 5 into the open space 3.

Two detector systems 6, 7 are arranged in the frame 2 (for example in its center region) that each have (outside of the open space 3) a radiation source 6a, 7a and an acquisition device 6b, 7b opposite said radiation source 6a, 7a and on the opposite side of the open space 3. The acquisition devices 6b, 7b respectively serve for acquisition of the detection radiation indicated by the arrows 6c, 7c. Both detector systems 6, 7 are arranged in the same transversal plane E.

The radiation sources 6a, 7a, for example, can be formed by a tube with a radiation region 6d, 7d directed toward the associated acquisition device 6b, 7b. Radiation beams proceeding from the radiation regions 6d, 7d transversely through the open space 3 respectively form detection regions 8, 9. The middle axes of the detection regions 8, 9 are directed transversely (in particular at right angles) to one another. This means that the detection regions 8, 9 intersect one another in a common section area.

The acquisition devices 6b, 7b can respectively be fashioned as segments (when viewed along the axis 3a of the open space 3), meaning that their length L in the circumferential direction can be greater than their breadth B in the longitudinal direction of the axis 3a. The detection regions 8, 9 emanating from the associated radiation sources 6a, 7a can be divergent, corresponding to the size (L×B) of the acquisition regions 6e, 7e facing towards the associated radiation source 6a, 7a.

The radiation sources 6a, 7a and acquisition devices 6b, 7b are supported by a movement device such that they can rotate around the axis 3a, for example, they can be pivoted or rotated back and forth. A suitable bearing arrangement can be, for example, a disc-shaped ring 10 shown in FIG. 2 on which the radiation sources 6a, 7a and the acquisition devices 6b, 7b can be attached so that can be moved in the circumferential direction into different positions (not shown). A drive 11 (for example an electromotor) advantageously serves for producing this movement (represented by the double arrow).

In operation of the apparatus 1, the detector systems 6, 7 are moved in the circumferential direction, and the radiation 6c, 7c proceed into the detection regions 8, 9 penetrates a patient located in the open space 3 in the region of a body part to be detected, and the attenuated radiation is acquired by the respective opposite acquisition region 6e, 7e and is graphically presented, for example on a film or image surface, for example, using associated measurement electronics.

The size of the detection region 8, 9 extending in the longitudinal direction of the axis 3a, namely known as the z-depth, is limited by the effective breadth B of the acquisition device 6b, 7b.

Figure 4:
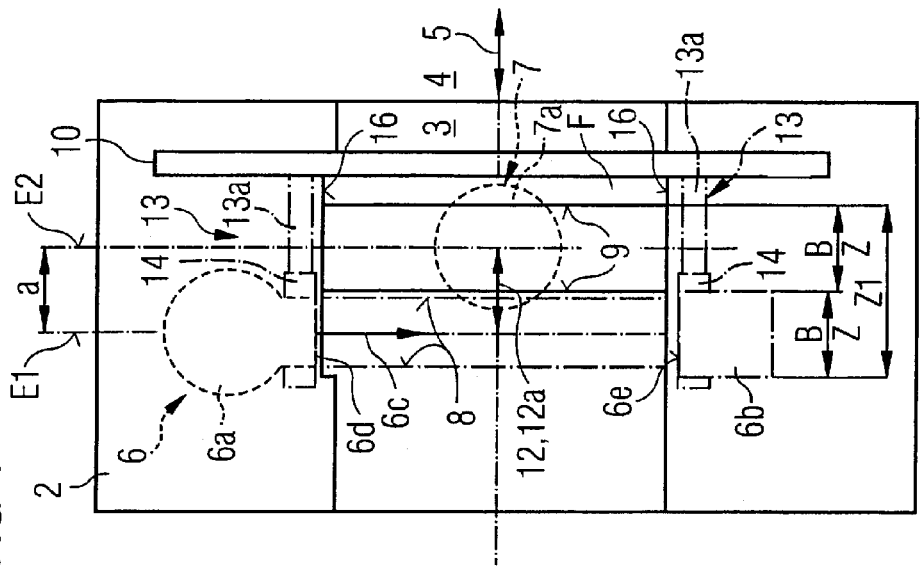
FIG. 4 shows the apparatus according to FIG. 3 in side view.
Figure 3:
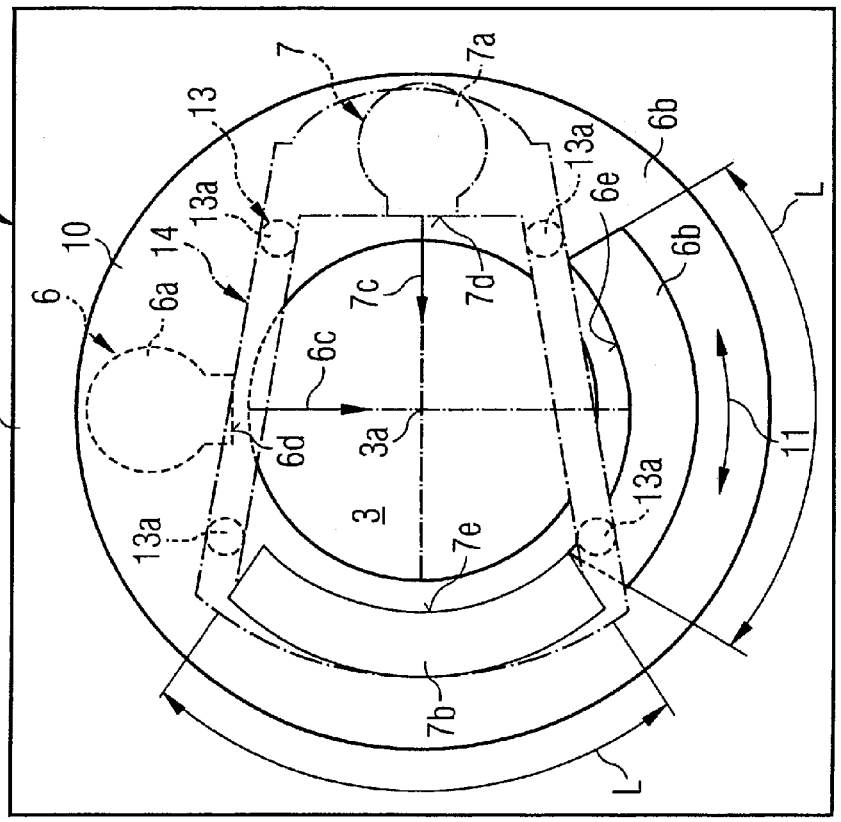
FIG. 3 shows an inventive apparatus for medical imaging in front view in a further embodiment.

In the exemplary embodiment according to FIG. 3 and FIG. 4 (in which the same or comparable parts are designated with the same reference characters), both detector systems 6, 7 are arranged offset relative to one another in longitudinal direction of the axis 3a or can be adjusted relative to one another in the longitudinal direction of the axis 3a and can be fixed in the respective adjustment position. This thus also applies for the associated detection regions 9, 8. In the shown position, the detector system 6 is displaced relative to the detector system 7 along the axis 3a until the detection regions 8, 9 or irradiation regions 6d, 7d lie immediately next to one another, or abut one another along the axis 3a.

In accordance with the invention, the axial separation a between the transverse center planes E1, E2 of the detector systems 6, 7 are dimensioned such that the irradiation regions 7d, 6d overlap one another or exhibit an axial separation from one another, the size of which, for example, is determined by the separation of two body parts or organs of the patient that are to be detected.

Due to the axially adjustable arrangement of the one detector system (here the detector system 6), this can be axially displaced (for example between an end position (not shown in FIG. 4) in which it is located in the transversal plane E2 with the detector system 7) by the amount a, and fixed in the position shown in FIG. 4. In the position shown in FIG. 4, the axial middle distance a (which corresponds to the z-depth in the exemplary embodiment, but can also be larger or smaller exists between the detector systems 6, 7. The adjustable detector system 6 can be displaced back and forth along the axis 3a by a displacement device 12 (indicated by a double arrow 12), in particular can be automatically displaced with a drive 12a that can be actuated in both axis directions (advantageously by an electric motor) and can be controlled or regulated via a control or regulation device (see FIG. 4).

The detector system 6 consequently can be axially displaced (relative to the detector system 7) into an alternative position in which either an enlarged z-depth results, or two z-depths axially spaced from one another yield a depth Z1 corresponding to their sum. In the exemplary embodiment according to FIG. 4, the z-depth Z1 is twice as large as in the exemplary embodiment according to FIG. 2.

The displacement device 12 for displacement of the displaceable detector system 6 has a guide 13 extending parallel to the axis 3a in the frame 2. The guide 13 can be formed by one or more guide rods 13a that can have, for example, a round cross-sectional shape. For a semi-automatic or wholly automatic displacement, a chassis 14 (for example in the form of a frame surrounding the open space 3) can be moved back and forth in a specific manner by the drive 12a on the at least one guide rod 13a. The displaceable detector system 6 is mounted on the chassis 14 or frame (see FIG. 4).

In accordance with the invention it is possible to mount the displaceable radiation source 6a and acquisition device 6b each on its own carrier part and to axially displace the radiation source 6a and acquisition device 6b with the carrier parts. In order to improve the alignment of the radiation source 6a and the acquisition device 6b directed toward one another and in order to simplify the bearing, it is more stable and better to mount the radiation source 6a and the acquisition device 6b on a common carrier, for example the frame-like chassis 14.

For example, the disc-shaped ring 10 on which the guide rods 13a are attached at one end can serve for bearing the aforementioned carrier parts or of the common carrier or chassis 14 on a rotatable or pivotable bearing part.

Figure 1:
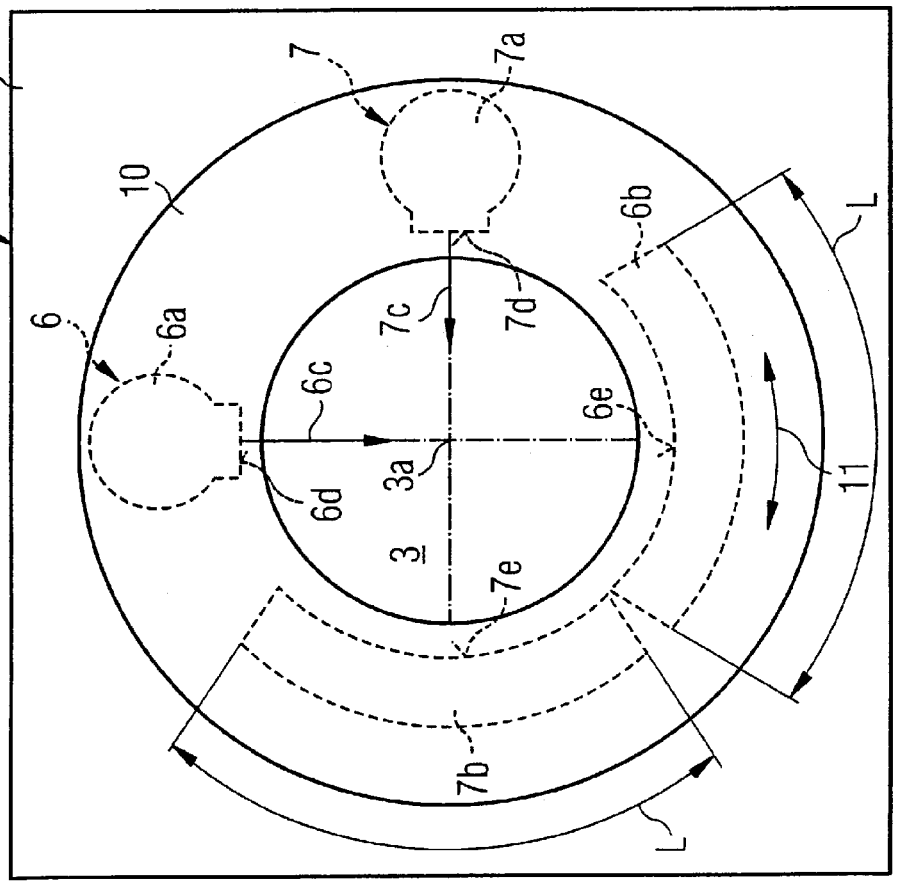
FIG. 1 shows an inventive apparatus for medical imaging in a schematic front view.

A further difference of the exemplary embodiment according to FIGS. 3 and 4 compared to that according to FIGS. 1 and 2 is that the detector system 7 (which cannot be displaced axially) exhibits an axial separation from its carrier, for example from the ring 10. An open space F that is advantageous for design reasons and in which, for example, electronic components can be arranged thus is formed between the detector system 7 and its carrier.

A mounting device for mounting of the radiation source 7a and acquisition device 7b is indicated by lines 16.

In the exemplary embodiments both detector systems 6, 7 can be moved in the circumferential direction via a common drive 11, for example by the ring 10.

Although modifications and changes may be suggested by those skilled in the art, it is the intention of the inventor to embody within the patent warranted hereon all changes and modifications as reasonably and properly come within the scope of his contribution to the art.

I claim as my invention:

1. An apparatus for medical imaging comprising:
an apparatus housing having an open space in an interior thereof that is open to one side of said apparatus housing, said open space having a longitudinal axis proceeding therethrough;
a first detector system disposed in said apparatus housing, comprising a first radiation source that emits first detection radiation, a first acquisition device that detects the first detection radiation, and having a first detection region that transversely proceeds through said open space;

a movement device in driving connection with said first detector system to move said first detector system in a circumferential direction of said open space;

a second detector system disposed in said apparatus housing, comprising a second radiation source that emits second detection radiation and a second acquisition device that detects the second detection radiation, and having a second detection region that transversely proceeds through said open space;

a movement device in driving connection with said second detector system that moves said second detector system in the circumferential direction of said open space;

a displacement device mechanically connected to each of said first and second detector systems that displaces said first and second detector systems relative to each other to cause said first and second detector systems to be selectively offset at different spacings from each other along said longitudinal axis, and that then fixes the first and second detector systems at respective positions along said longitudinal axis; and a displacement guide, substantially parallel to said longitudinal axis, mounted in said apparatus housing in a circumferential region of said open space, comprising a plurality of guide rods distributed around a circumference of said open space and proceeding parallel to said longitudinal axis, and a first chassis at which said first detector system is mounted and a second chassis at which said second detector system is mounted, each of said first chassis and said second chassis having a plurality of openings therein distributed a periphery thereof that respectively receives said guide rods to guide displacement of said first and second detector systems along said longitudinal axis.

2. An apparatus as claimed in claim 1 wherein said displacement device comprises a motor-actuated drive.

* * * * *